(12) United States Patent
Kato et al.

(10) Patent No.: US 6,413,747 B1
(45) Date of Patent: *Jul. 2, 2002

(54) ENHANCEMENT OF NUCLEIC ACID AMPLIFICATION BY THE ADDITION OF A POLYAMINE

(75) Inventors: Shingo Kato, Tokyo; Naoyuki Nishimura, Kyoto, both of (JP)

(73) Assignee: Shimadzu Corporation, Kyoto (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 51 days.

(21) Appl. No.: 08/928,679

(22) Filed: Sep. 12, 1997

Related U.S. Application Data (63) Continuation of application No. 08/669,977, filed on Jun. 25, 1996, now abandoned, which is a continuation-in-part of application No. 08/316,783, filed on Oct. 3, 1994, now abandoned.

(51) Int. Cl.$^7$ .......................... C12P 19/34; C07H 21/02; C07H 21/04
(52) U.S. Cl. ..................... 435/91.2; 536/23.1; 536/24.3
(58) Field of Search .............................. 435/91.1, 91.2, 435/6; 536/23.1, 24.3; 935/76, 77, 78

(56) References Cited

U.S. PATENT DOCUMENTS

| | | | | |
|---|---|---|---|---|
| 5,278,298 A | * | 1/1994 | Chakraborty et al. | ..... 536/24.32 |
| 5,298,392 A | * | 3/1994 | Atlas et al. | |
| 5,525,492 A | * | 6/1996 | Hill | ........................... 435/91.2 |

FOREIGN PATENT DOCUMENTS

| | | | |
|---|---|---|---|
| EP | 439208 A2 | * | 7/1991 |
| WO | WO9217609 | * | 10/1992 |

OTHER PUBLICATIONS

Frankel et al., J. of Infectious Diseases 161 :1252–1256 (1990).*
Widjojcatmodjo et al., J. of Clinical Microbiology 30(12): 3195–3199 (1992).*
Jang et al., J. of Clinical Microbiology 30(10): 2529–2534 (1992).*
Hoss et al., Nature 359 :199 (1992).*
Cave et al., Bio Techniques 16(5) : 809–810 (May 1994).*
Gumerlock et al., Reviews of Infectious Diseases 13 : 1053–1060 (1991).*
Abede et al., Scand J of Infectious Disease 24 : 265–273 (1992).*
Varela et al., J. of Clinical Microbiology 32(5) : 1246–1248 (May 1994).*
Wan, C. and Wilkins, T. (1993) PCR methods and applications 3: pp. 208–210.*
Barany, F. (1991) Proc. Natl. Acad. Sci., USA 88 : pp. 189–193.*
Tabor, C. and Tabor, H. (1976) Annu. Rev. Biochem. 53: pp. 749–790.*
Fisher, P. and Korn, D. (1979) J. Biol. Chem. 254: pp. 11033–11039.*
Pommier, Y et al. (1989) Biochemistry 28: pp. 995–1002.*
Raskin et al. (1992) PCR Methods and Applications 2(2):154–156, Apr. 9, 1997.*

* cited by examiner

Primary Examiner—Ethan C. Whisenant
(74) Attorney, Agent, or Firm—Beyer Weaver & Thomas, LLP (57) ABSTRACT

If polyamine is caused to be present in the reacting system for the synthesis of nucleic acids to amplify target genes from a sample, the inhibition of the synthesis due to impurities in the sample can be reduced and the target genes can be effectively synthesized.

2 Claims, 9 Drawing Sheets

Ethylenediamine

FIG._6A

Trimethylenediamine

FIG._6B

Putrescine

FIG._6C

Diethylenetriamine

FIG._6D

Spermidine

FIG._6E

Triethylenetetramine

FIG._6F

Spermine

FIG._6G

Tetraethylenepentamine

FIG._6H

Pentaethylenehexamine

FIG._6I

Ethylenediamine

FIG._7A

Trimethylenediamine

FIG._7B

Putrescine

FIG._7C

Diethylenetriamine

FIG._7D

Spermidine

FIG._7E

Triethylenetetramine

FIG._7F

Spermine

FIG._7G

Tetraethylenepentamine

FIG._7H

Pentaethylenehexamine

FIG._7I

None

FIG._7J

Ethylenediamine
*FIG._8A*

Trimethylenediamine
*FIG._8B*

Putrescine
*FIG._8C*

Diethylenetriamine
*FIG._8D*

Spermidine
*FIG._8E*

Triethylenetetramine
*FIG._8F*

Spermine
*FIG._8G*

Tetraethylenepentamine
*FIG._8H*

Pentaethylenehexamine
*FIG._8I*

Ethylenediamine
FIG._9A

Trimethylenediamine
FIG._9B

Putrescine
FIG._9C

Diethylenetriamine
FIG._9D

Spermidine
FIG._9E

Triethylenetetramine
FIG._9F

Spermine
FIG._9G

Tetraethylenepentamine
FIG._9H

Pentaethylenehexamine
FIG._9I

None Addition
FIG._9J

Ethylenediamine
FIG._10A

Trimethylenediamine
FIG._10B

Putrescine
FIG._10C

Diethylenetriamine
FIG._10D

Spermidine
FIG._10E

Triethylenetetramine
FIG._10F

Spermine
FIG._10G

Tetraethylenepentamine
FIG._10H

Pentaethylenehexamine
FIG._10I

Ethylenediamine

FIG._11A

Trimethylenediamine

FIG._11B

Putrescine

FIG._11C

Diethylenetriamine

FIG._11D

Spermidine

FIG._11E

Triethylenetetramine

FIG._11F

Spermine

FIG._11G

Tetraethylenepentamine

FIG._11H

Pentaethylenehexamine

FIG._11I

None Addition

FIG._11J

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "SYNTHESIZED DNA"

(iv) ANTI-SENSE: NO (xi) SEQUENCE DESCRIPTION: SEQ ID NO: 1:

GTTAGGCGTG CAAAGGCCAA G                                           21

(2) INFORMATION FOR SEQ ID NO: 2:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "SYNTHESIZED DNA"

(iv) ANTI-SENSE: NO (xi) SEQUENCE DESCRIPTION: SEQ ID NO: 2:

GCGTATTAAT CCCGTAGGTC                                             20

(2) INFORMATION FOR SEQ ID NO: 3:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "SYNTHESIZED DNA"

(iv) ANTI-SENSE: NO (xi) SEQUENCE DESCRIPTION: SEQ ID NO: 3:

GCACAGCTGT GTTTACTAGC                                             20

(2) INFORMATION FOR SEQ ID NO: 4:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "SYNTHESIZED DNA"

(iv) ANTI-SENSE: NO (xi) SEQUENCE DESCRIPTION: SEQ ID NO: 4:

CACATACCTC CTTCCACTCG                                             20

ENHANCEMENT OF NUCLEIC ACID AMPLIFICATION BY THE ADDITION OF A POLYAMINE

This is a continuation of application Ser. No. 08/669,977 filed Jun. 25, 1996, now abandoned, which is a continuation-in-part of application Ser. No. 08/316,783 filed Oct. 3, 1994, now abandoned.

BACKGROUND OF THE INVENTION

This invention relates to synthesis of nucleic acids, and more particularly to synthesis of nucleic acids by a polymerase chain reaction method.

The polymerase chain reaction (hereafter PCR) method is one of the techniques for amplifying genes. By this method, a particular segment of target DNA (template DNA) can be amplified by a factor of hundreds of thousands, and this is accomplished with a pair of primers sandwiching target DNA regions and by repeating reactions consisting of denaturation, annealing and polymerization of DNA. The PCR is usually used for the analysis of an extremely small amount of DNA, for example, from one virus, one bacterium or one cell in samples under investigation.

For the analysis of nucleic acids of viruses, bacteria or cells contained in samples from living organisms (such as tissue, blood, marrow fluid, sputum, milk, urine and feces of an animal or roots, stems, leaves, flowers and fruits of a plant), an environmental sample (such as soil and water) or a food sample (such as meats, milk and eggs), however, it is necessary to first remove impurities in the sample and to separate and purify the nucleic acids. A commonly practiced method for this process at the present time is to first treat the sample with an enzyme or a surfactant and then to use a phenol-chloroform mixture. More recent methods of purifying DNA include the removal of impurities by using ion exchange resins, glass beads and agents for protein separation. By any of these methods, however, it is difficult to sufficiently remove the impurities, and this frequently causes to inhibit the amplification of genes by a method of synthesizing nucleic acids such as the PCR method.

Hypothesizing that the addition of polyamine during gene amplification might reduce the inhibition of the synthesis of nucleic acids by impurities, the present inventors extensively reviewed available documents and reports. Wan and Wilkins (PCR Methods and Applications, 3, 208-210 (1993)) reported that spermidine, which is a kind of polyamines, facilitates PCR amplification of high-quality genomic DNA purified from cotton leaves by tedious purification procedures and that optimum spermidine concentrations are 0.2–1 mM, but there has not been any report describing that the addition of polyamine could reduce the inhibition of the synthesis of nucleic acids by impurities contained in samples or low-quality DNA purified from samples by rough purification procedures.

SUMMARY OF THE INVENTION

It is therefore an object of this invention to provide methods of synthesizing nucleic acids from a sample which is likely to inhibit synthesis of nucleic acids, that is, a crude sample obtained from materials derived from living organisms.

For the purpose of attaining the aforementioned object, the present inventors investigated whether polyamine reduced the inhibition of nucleic acid synthesis by the existence of impurities by adding various kinds of polyamine at various concentrations to crude samples from materials such as human feces and blood, and thereafter using a PCR method to carry out the synthesis of nucleic acids. As a result, it was discovered that the inhibition of nucleic acid synthesis by impurities in the sample can be reduced if any of various kinds of polyamine is added at a concentration within a certain range.

BRIEF DESCRIPTION OF THE DRAWINGS

The accompanying drawings, which are incorporated in and form a part of this specification, illustrate effects of the invention and, together with the description, serve to explain the principles of the invention. In the drawings.

DETAILED DESCRIPTION OF THE INVENTION

This invention relates to a method of synthesizing nucleic acids for amplifying target gene from a sample, characterized by the step of adding polyamine into a reaction mixture.

Examples of the sample which may be used according to this invention include unrefined (impurity-containing) samples from a living organism such as tissues, blood, marrow fluid, sputum, milk, urine and feces of an animal or roots, stems, leaves, flowers and fruits of a plant, environmental samples such as soils and water, and food samples such as meats, milk and eggs, but the invention is not limited by these examples.

Examples of the polyamine according to the present invention include all hydrocarbons having two or more primary or secondary amino groups. As long as they are a hydrocarbon having two or more of primary or secondary amino groups within the molecule, there are no particular limitations imposed thereon. Examples of such polyamine according to the invention include ethylene diamine, trimethylene diamine, spermine, spermidine, diethylene triamine, triethylene tetramine, tetraethylene pentamine, pentaethylene hexamine, 1,4-bis(3-aminopropyl)-piperadine, 1-(2-aminoethyl)piperadine, 1-(2-aminoethyl) piperidine, 1,4,10,13-tetraoxa-7,16-diazacyclooctadecane, and tris(2-aminoethyl)amine.

Throughout herein, improved methods according to this invention for synthesizing nucleic acids relate to ordinary methods of synthesis such as the PCR method, not limited to any particular method. In what follows, a method according to this invention will be described with reference to the PCR method. In the description that follows, furthermore, "PCR core solution" shall mean any basic reaction liquid for PCR, containing various kinds of primers and deoxyribonucleotide triphosphates (dNTP: dATP, dGTP, dCTP, dTTP, DNA polymerase and salts), and "PCR reaction solution"

shall mean any mixtures of a sample solution, a PCR core solution and polyamine.

According to the present invention, polyamine is added to a reacting system. There are no particular limitations regarding the manner in which this addition should take place, as long as the PCR reaction takes place in the presence of polyamine. For example, it may be added together with a sample solution (such as an extract from feces) into a PCR core solution immediately before PCR. As another example, it may be added preliminarily when the sample solution or the PCR core solution is being prepared.

The amount of polyamine to be added (or its concentration) varies according to the kind of the polyamine to be added and the kind and the concentration of the sample solution, but it is about 0.01–10 mM in general in the PCR reaction solution. The concentration should preferably be 0.5–4 mM.

The procedure for the PCR method of the present invention is different from the ordinary method principally in that polyamine is added into the reaction mixture. In the first step, single-strand DNA is obtained by thermal denaturation from double-strand DNA. In the next process, primers of about 20 base pairs sandwiching the segments to be amplified are annealed to the single-strand DNA, and it is followed by the polymerization process wherein the primers are extended by the function of DNA polymerase in the presence of four kinds of dNTP. If the series of processes described above is repeated in cycles, the desired DNA fragment is amplified exponentially as $2^n$ (where n is the number of repeated cycles) at least in theory. Thermostable DNA polymerases are usually used for the extension reaction of primers.

The amount of target DNA in a sample used for PCR is from ag order to $\mu$g order, and the concentration of the primer is appropriately determined according thereto. The conditions for the PCR vary according to the sequence of the primers, but the denaturation process usually takes about 0.25–1 minute at 90–97° C., the annealing process about 0.5–3 minutes at 40–75° C. and the polymerization process usually 0.5–3 minutes at 55–75° C. The optimum number of cycles of these processes depends on the initial concentration of the target DNA in the sample but it is usually 25–45.

Various known methods may be used for the detection of amplified DNA fragments, such as a method of agarose gel electrophoresis, or a method of hybridization by using a labeled probe.

In what follows, the invention will be explained further in detail by way of examples, but the scope of the invention is not intended to be limited by these examples.

EXAMPLE NO. 1

A sample of human feces 100 mg was dissolved by using 0.1 M EDTA (ethylenediaminetetraacetic acid) and 0.1% SDS (sodium laurylsulfate) and extracted by using a phenol-chloroform mixture. After the process of the phenol-chloroform extract, ethanol was used for precipitation and 70% ethanol was used for desalting. After a drying process, the sample was dissolved in 1 ml of TE (10 mM of tris-HCl, 1 mM of EDTA, pH 8.0). The extract which was colored light brown indicated existence of much contamination of impurities for rough purification method. PCR was carried out after DNA (100 copies) of Agrobacterium rhizogenes A4 strain (hereafter simply as A4 strain) as template DNA, a variety of polyamine and PCR core solution were added to this extract.

The primers for the PCR were oligonucleotide ($P_1$, sequence number=1) homologous to plus-chain and oligonucleotide ($P_2$, sequence number=2) homologous to minus-chain, which are located in rol A coding region of the A4 strain and what gives 202 bp PCR products: where $P_1$: 5'GTTAGGCGTGCAAAGGCCAAG 3'  (SEQ ID No. 1)

$P_2$: 5'GCGTATTAATCCCGTAGGTC 3'  (SEQ ID No. 2)

The PCR core solution was made of reaction mixtures 10 mM of tris-HCl with pH 8.3; 50 mM of KCl; 1.5 mM of $MgCl_2$; 0.01% (w/v) gelatine and 0.025 units/$\mu$l of thermostable DNA polymerase (AmpliTaq, produced by Perkin Elmer Cetus) containing 1 $\mu$M of each primer and 200 $\mu$M of four kinds of dNTP. The total amount of the PCR reaction solution was 30 $\mu$l, with 3 $\mu$l each of the extract from feces, the DNA of the A4 strain and polyamine solution being added thereto.

After a thermal denaturation process of 1 minute and 30 seconds at 94° C., 40 cycles of PCR was carried out, each cycle including thermal denaturation for one minute at 94° C., annealing for one minute at 55° C. and primer extension for one minute at 72° C. After the 40th cycle, the primer extension was carried out for an additional period of 7 minutes to ensure that the amplified DNA was double stranded. PCR-amplified DNAs were detected by agarose gel electrophoresis. A 5 $\mu$l portion of the PCR-amplified mixture was separated in 3% agarose gel by electrophoresis at 3–4 $Vcm^{-1}$ for one hour in TAE buffer (40 mM tris-acetate, 1 mM EDTA, pH 8.0) containing 0.5 $\mu$g/ml ethidium bromide.

Next, the results according to Example No. 1 are described with reference to FIGS. 1, 2 and 3, which show the results of PCR by mixing 3 $\mu$l of extract which was obtained from 100 mg of human feces by the phenolchloroform method and dissolving in 1 ml of TE, 3 $\mu$l (100 copies) of purified DNA of A4 strain and 3 $\mu$l of various kinds of polyamine solution and thereafter adding 21 $\mu$l of PCR core solution. In each figure, the amount of added polyamine was different, depending on the lane. Polyamine was added such that the final concentration should be 10 mM in Lane 1, 3.2 mM in Lane 2, 1 mM in Lane 3, 0.32 mM in Lane 4, 0.1 mM in Lane 5, 0.032 mM in Lane 6 and 0.01 mM in Lane 7. Lane SC indicates a sample control wherein 3 $\mu$l of distilled water was added, instead of polyamine, into the core solution. Lane PC indicates a positive control with TE and distilled water added to the core solution instead of the extract from feces and polyamine, respectively. Lane NC indicates a negative control with TE and distilled water added to the core solution instead of the extract from feces, purified DNA from the A4 strain and polyamine. Lane M indicates a molecular weight marker (Hinc II-digested $\phi$x174 RF DNA).

Figure 1:
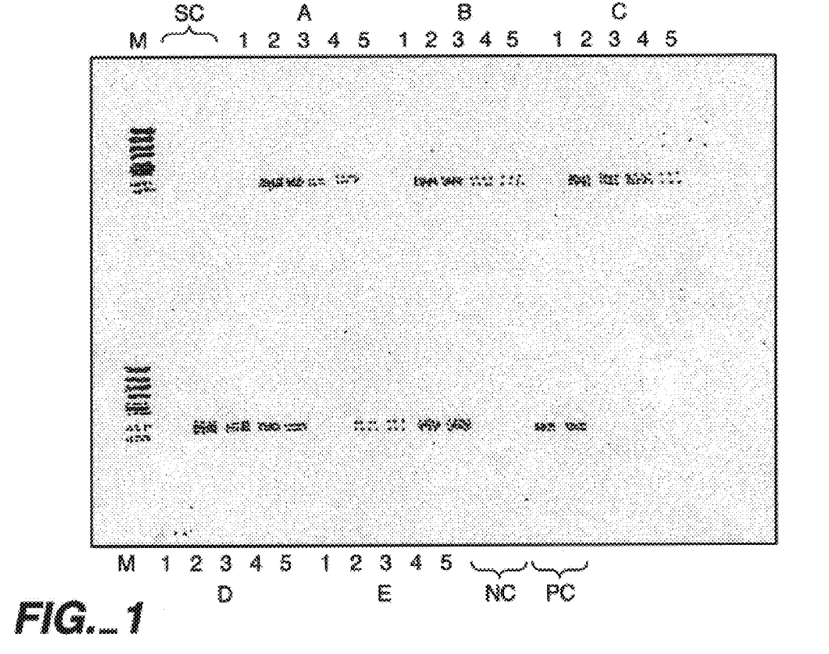
FIGS. 1–3 are the agarose gel analyses of products of PCR with different kinds of polyamine added to extract from feces at different concentrations.
Figure 2:
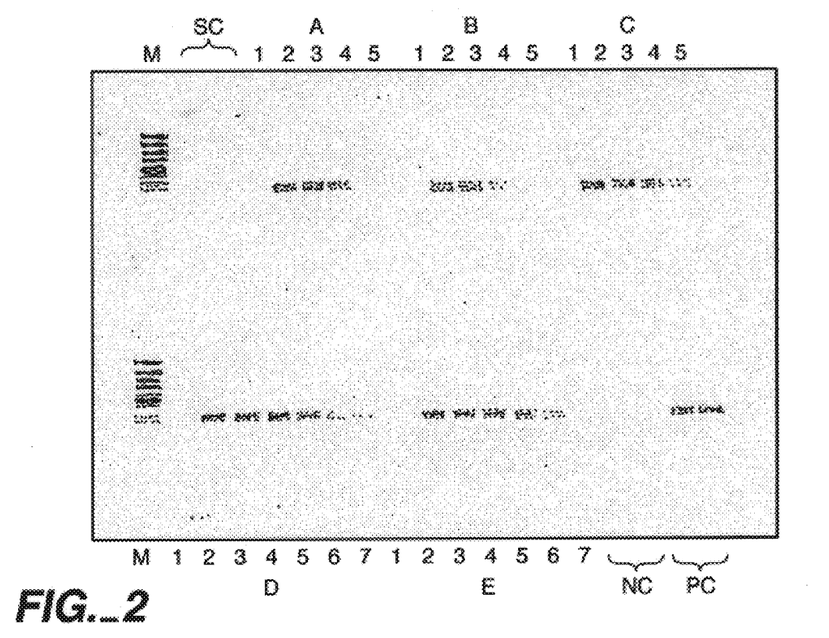
Figure 3:
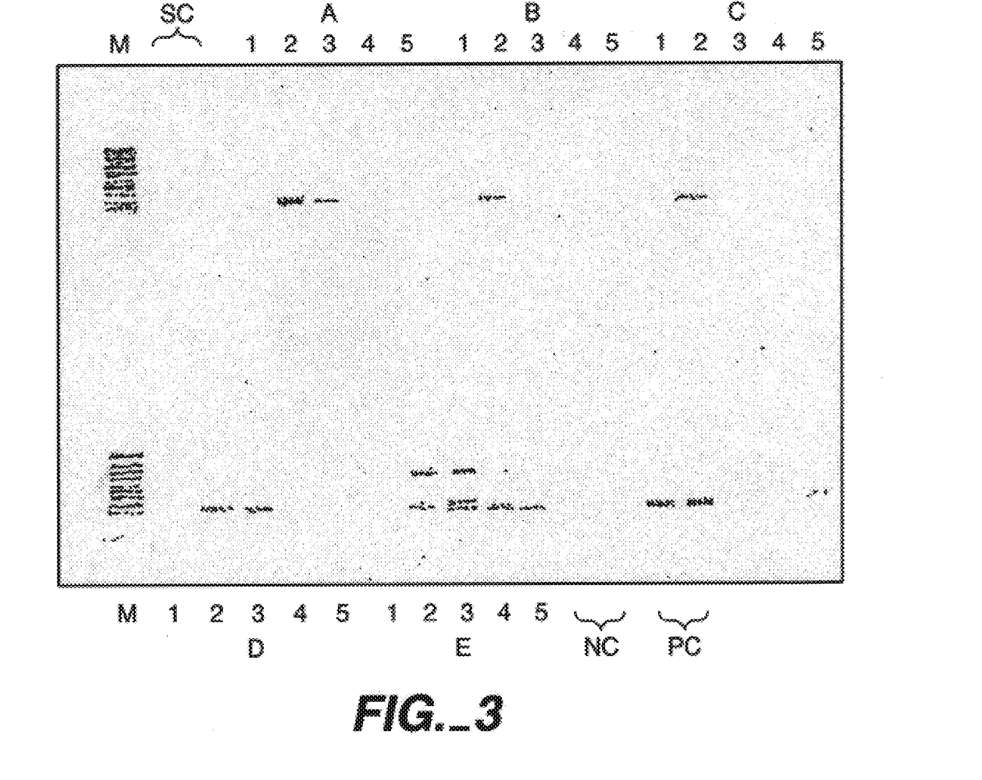

In FIGS. 1, 2 and 3, letters A–E indicate the kinds of polyamine that was used. In FIG. 1, A–E respectively indicate ethylene diamine (A), trimethylene diamine (B), spermidine (C), triethylene tetramine (D) and spermine (E). In FIG. 2, A–E respectively indicate spermidine (A), diethylene triamine (B), triethylene tetramine (C), tetraethylene pentamine (D) and pentaethylene hexamine (E). In FIG. 3, A–E respectively indicate 1,4-bis(3-aminopropyl)-piperadine (A), 1-(2-aminoethyl)piperadine (B), 1-(2-aminoethyl)piperidine (C), 1,4,10,13-tetraoxa-7-16-diazacyclooctadecane (D) and tris(2-aminoethyl)amine (E).

FIGS. 1, 2 and 3 show that amplification reaction is inhibited in Lanes SC and no PCR products are detected but that the inhibition of the amplification reaction by the presence of impurities derived from the feces is reduced by the addition of polyamine.

EXAMPLE NO. 2

Used as the sample was 23 µl of human blood (with 6000 white blood cells/microliter) into which 5 µl of mouse blood, diluted step-wise with a phosphate buffer, was added. After the sample was subjected to a lysis process of red blood cells, the white blood cells were precipitated by centrifugation and the supernatant was removed. Polyamine and PCR core solution were added to the precipitated white cells. The primers for the PCR were oligonucleotide ($P_3$, sequence number=3) homologous to plus-chain and oligonucleotide ($P_4$, sequence number=4) homologous to minus-chain, which are located in the β-globin coding region of the mouse and what gives 174 bp PCR products: where

| | | |
|---|---|---|
| $P_3$: | 5'GCACAGCTGTGTTTACTAGC 3' | (SEQ ID No. 3) |
| $P_4$: | 5'CACATACCTCCTTCCACTCG 3' | (SEQ ID No. 4) |

Figure 4:
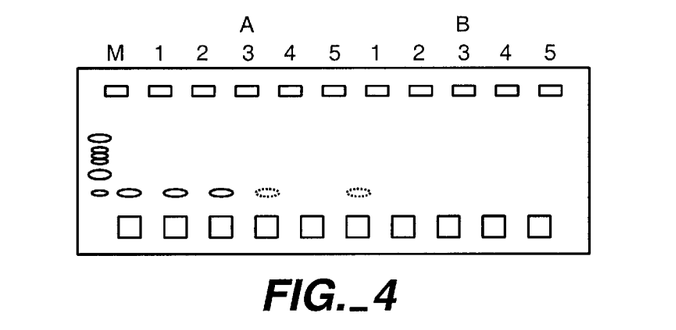
FIG. 4 is the agarose gel analysis of products of PCR with peripheral blood leucocytes derived from sequentially diluted blood of a mouse added to human blood (at different concentrations of white blood cells of the mouse) with and without the addition of 2 mM of spermidine into the reaction mixture.

The same PCR core solution was used as in Example No. 1 except that the primers were $P_3$ and $P_4$. The total amount of the PCR reaction solution was 100 µl, and 10 µl of spermidine solution (final concentration: 2 mM) was added. PCR and detection of amplified DNA were carried out as in Example No. 1. The results of this Example are shown in FIG. 4, wherein A indicates a group to which polyamine and PCR core solution were added and B indicates a group to which only PCR core solution was added. Lanes 1–5 respectively show the results when the number of white blood cells of the mouse added into the PCR tube was $10^4$ (Lane 1), $10^3$ (Lane 2), $10^2$ (Lane 3), 10 (Lane 4), and zero (Lane 5). Lane M indicates a molecular weight marker. FIG. 4 clearly shows the effects of adding polyamine. In Group B wherein only a PCR core solution is added, the amplification reaction is strongly inhibited and a thin band of amplified DNA is observable only in Lane 1 where as many as $10^4$ white blood cells of the mouse were present. If polyamine is added (Group A), by contrast, the inhibition of the amplification reaction is effectively removed, and the presence of PCR products can be detected if there are as few as about ten white blood cells of the mouse without any purification of DNA.

EXAMPLE NO. 3

Used as the sample was 100 mg of sandy soil from a rice field or 100 mg of homogenized tobacco leaf. The sample was dissolved with 0.1 M EDTA and 0.1% SDS, purified with weakly negative ion-exchange resin (DEAE-Sepharose, fast flow (Pharmacia)), and eluted with 400 µl of 10 mM of tris-HCl (pH 7.0) containing 1 M NaCl. The extract which was colored light brown or light green indicated existence of much contamination of impurities for rough purification material. PCR was carried out after polyamine and PCR core solution were added to the extract. PCR core solution was prepared by removing KCl from the core solution used in Example No. 1. The amount of the PCR core solution was 24 µl, and 3 µl each of DNA-containing extract and spermidine solution was added thereto. PCR and detection of amplified DNA was carried out as in Example No. 1. The results are shown in FIG. 5.

Figure 5:
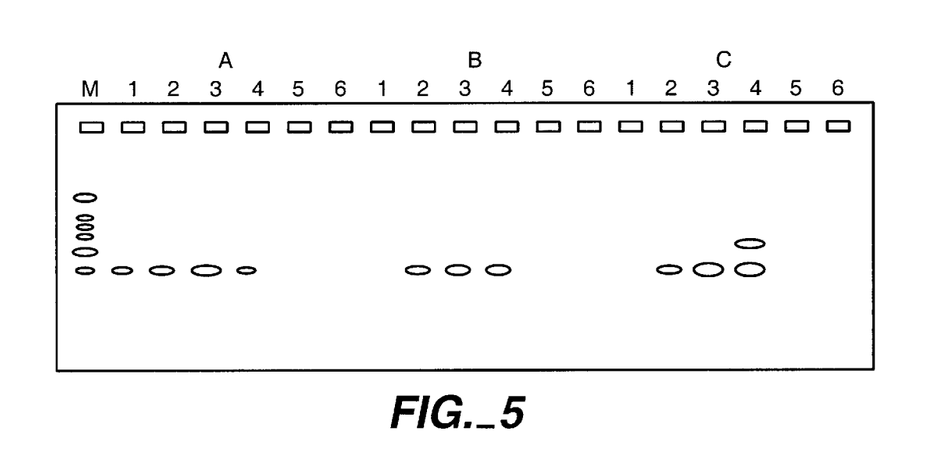
FIG. 5 is the agarose gel analysis of products of PCR with spermidine added to extract from leaves and soil at different concentrations to the reaction mixture.
Figure 6A:
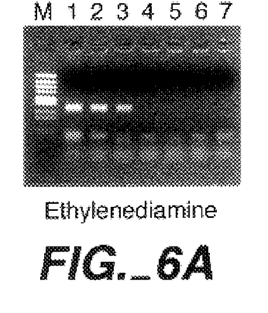
FIGS. 6, 7, 8, 9, 10 and 11 are the results of further tests on the effects of various polyamines for reducing inhibition of PCR by impurities in blood, feces and urine samples without purification of DNA.
Figure 6B:
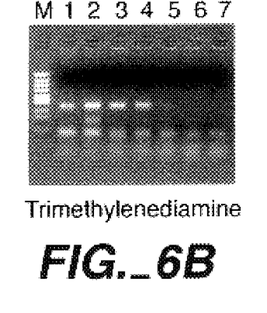
Figure 6C:
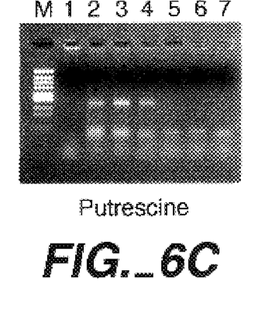
Figure 6D:
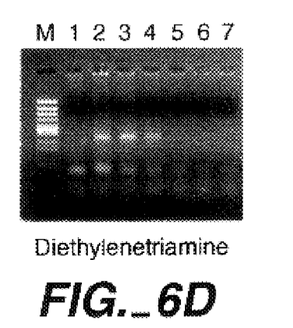
Figure 6E:
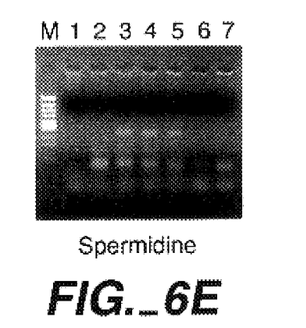
Figure 6F:
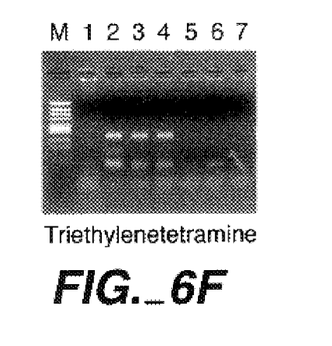
Figure 6G:
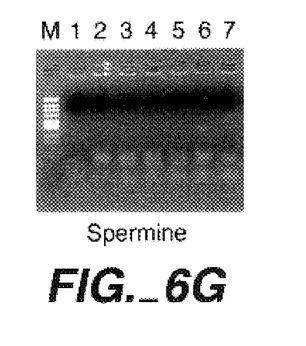
Figure 6H:
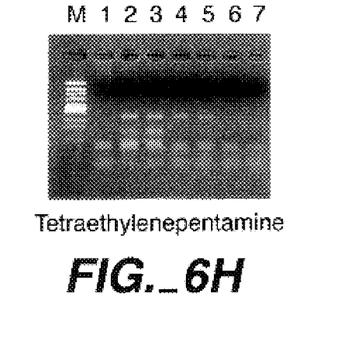
Figure 6I:
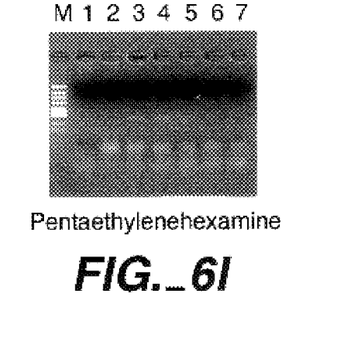
Figure 7A:
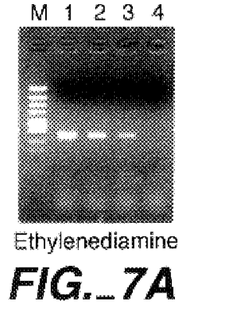
Figure 7B:
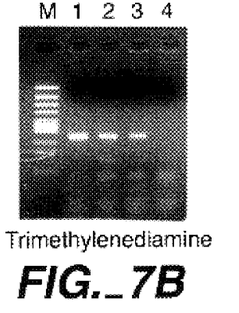
Figure 7C:
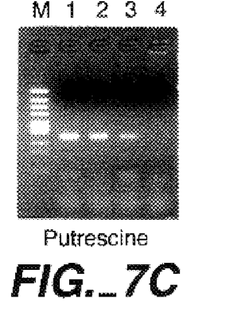
Figure 7D:
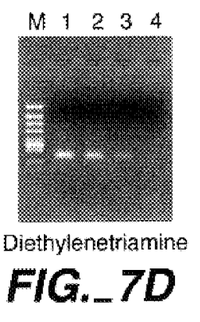
Figure 7E:
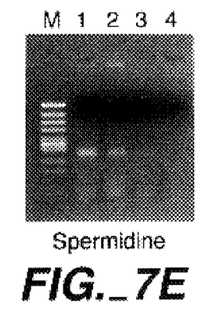
Figure 7F:
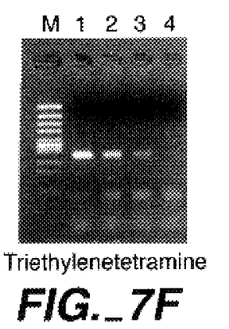
Figure 7G:
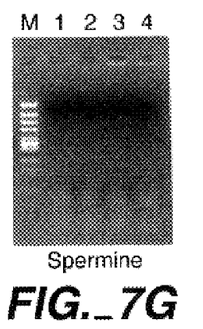
Figure 7H:
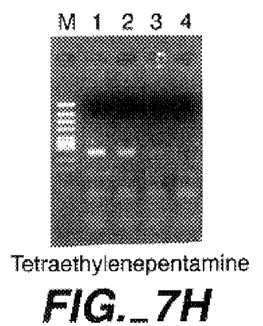
Figure 7I:
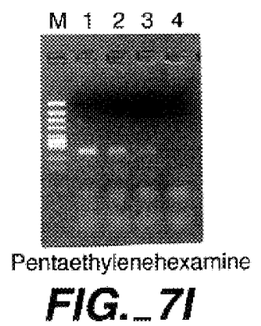
Figure 7J:
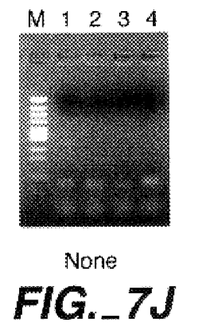
Figure 8A:
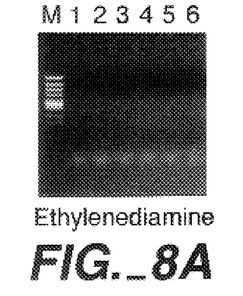
Figure 8B:
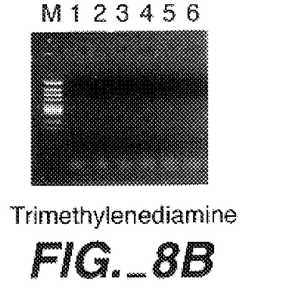
Figure 8C:
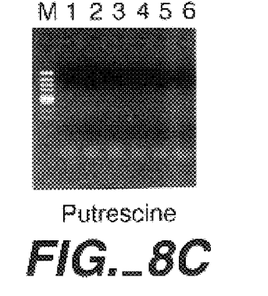
Figure 8D:
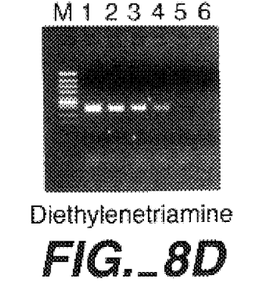
Figure 8E:
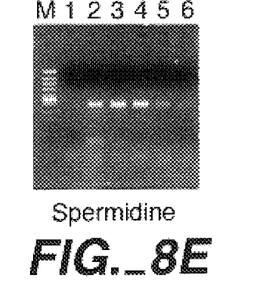
Figure 8F:
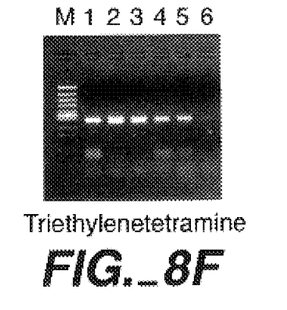
Figure 8G:
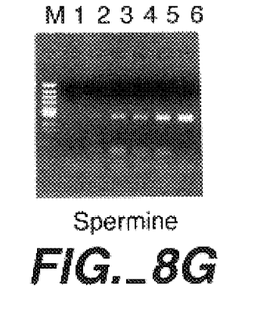
Figure 8H:
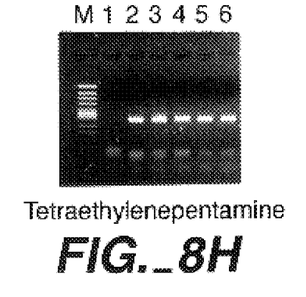
Figure 8I:
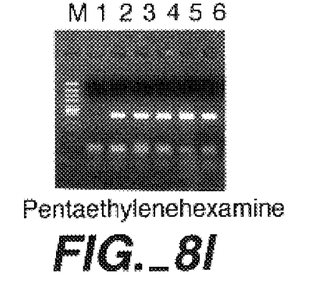
Figure 9A:
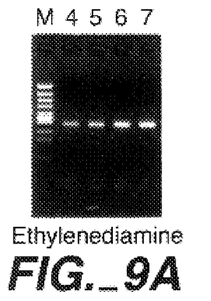
Figure 9B:
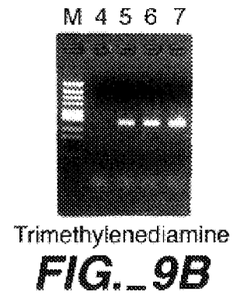
Figure 9C:
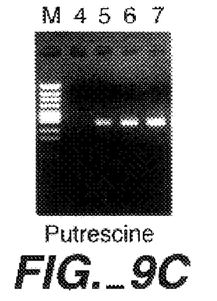
Figure 9D:
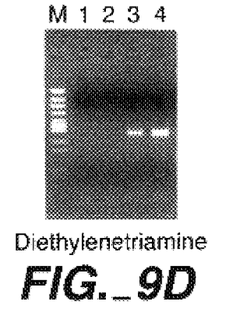
Figure 9E:
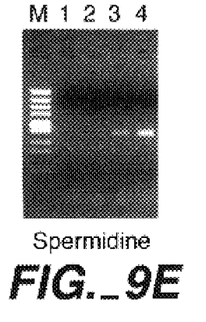
Figure 9F:
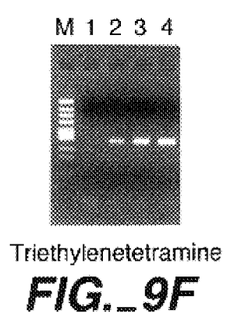
Figure 9G:
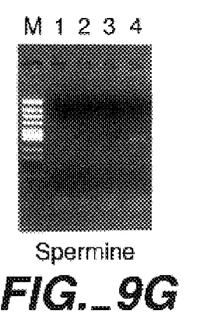
Figure 9H:
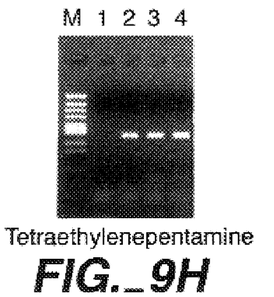
Figure 9I:
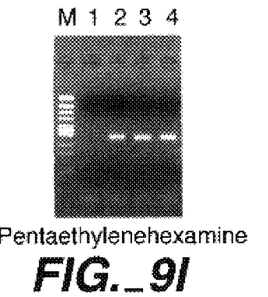
Figure 9J:
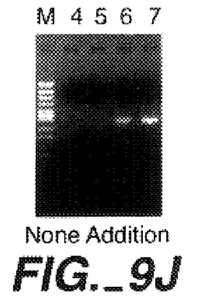
Figure 10A:
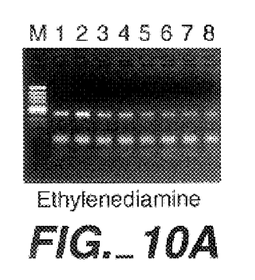
Figure 10B:
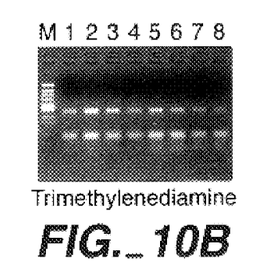
Figure 10C:
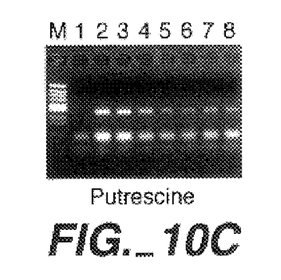
Figure 10D:
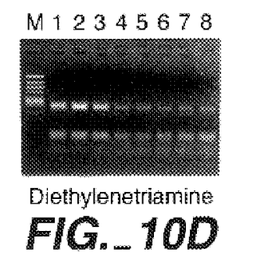
Figure 10E:
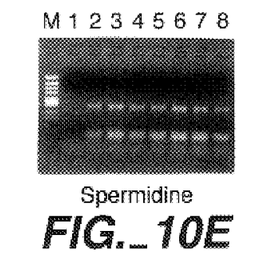
Figure 10F:
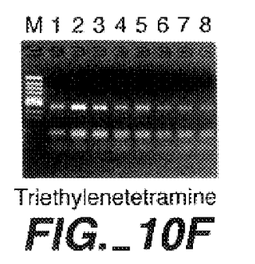
Figure 10G:
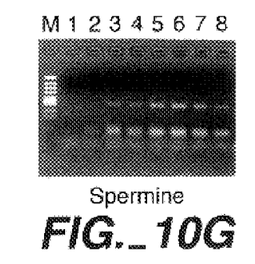
Figure 10H:
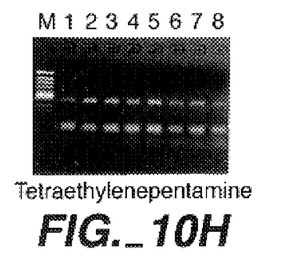
Figure 10I:
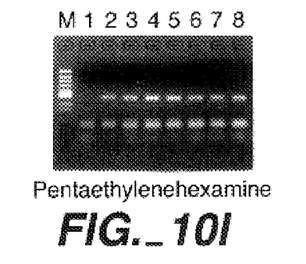
Figure 11A:
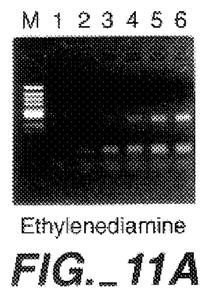
Figure 11B:
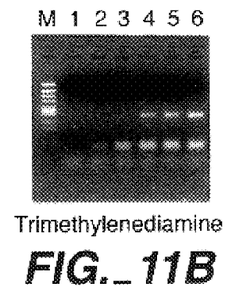
Figure 11C:
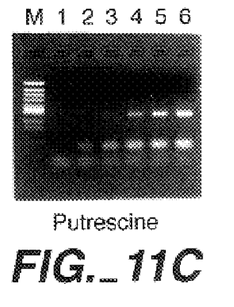
Figure 11D:
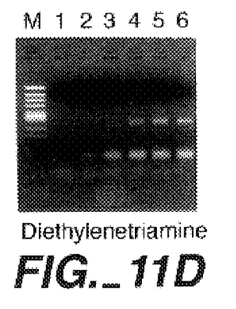
Figure 11E:
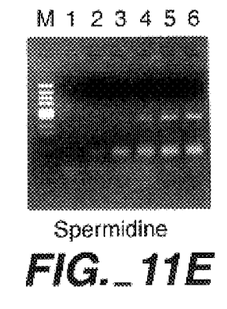
Figure 11F:
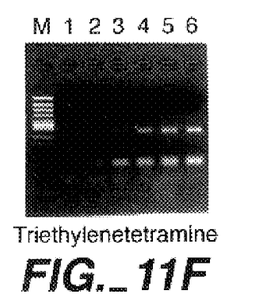
Figure 11G:
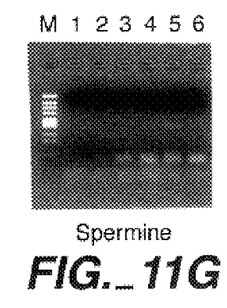
Figure 11H:
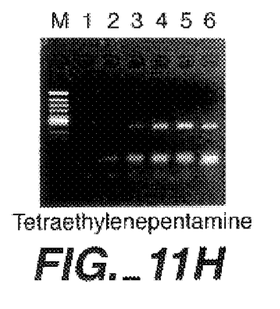
Figure 11I:
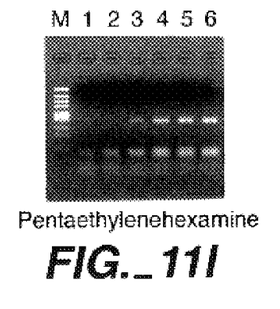
Figure 11J:
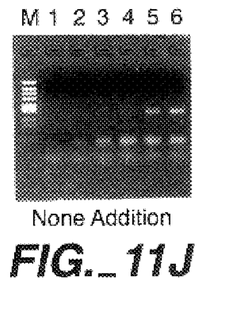

In FIG. 5, A indicates a positive control group containing only DNA, B indicates a group with soil extract mixed thereto, and C indicates a group with a tobacco leaf extract mixed thereto. The final concentration of polyamine was zero in Lane 1, 0.5 mM in Lane 2, 1 mM in Lane 3, 2 mM in Lane 4, 4 mM in Lane 5 and 8 mM in Lane 6. Lane M indicates a molecular weight marker.

Lanes 1 of Groups B and C show that the amplifying reaction is inhibited when an extract from soil or a leaf is added since no PCR products are detected. As seen in Lanes 2–4 of Groups B and C, however, such inhibition is removed. PCR products can be detected if polyamine is added at a concentration of 0.5–2 mM.

In view of the aforementioned report by Wan and Wilkins, the following six experiments were also conducted to test the effects of various polyamines for reducing inhibition of PCR by impurities in blood, feces and urine samples.

Experiment No. 1 (With Human Blood)

White blood cells were obtained by taking 14 µl ($7 \times 10^4$ WBC) of human blood, centrifuging it and removing therefrom the supernatant. Various kinds of polyamine, HIV DNA (100 copies/tube) and PCR core solution were added to the white blood cells thus collected for carrying out PCR (total 50 µl). The primers for the PCR were oligonucleotide ($P_5$) homologous to plus-chain and oligonucleotide ($P_6$) homologous to minus chain, which are located in Reverse transcriptase coding region of the HIV-1 strain and what gives 231 bp PCR products (See Simmons, P. et al.: J. Virol. 64, 864–872, 1990): where

| | | |
|---|---|---|
| $P_1$: | 5'CATGGGTACCAGCACACAAAGG 3' | (SEQ ID No. 5) |
| $P_2$: | 5'TCTACTTGTCCATGCATGGCTTC 3' | (SEQ ID No. 6) |

Use as PCR core solutions was made of reaction mixtures (10 mM Tris-HCl, pH 8.3; 50 mM KCl; 1.5 mM $MgCl_2$; 1.25 U Taq polymerase (TaKaRa tag, produced by Takara Shuzo Co., Ltd. of Japan)) containing 1 µM of each primer and 200 µM of 4 kinds of dNTP.

After a preheating process of 4 minutes at 94° C., the PCR was carried out for 50 cycles under the conditions of 94° C. for 30 seconds, 60° C. for 1 minute and 72° C. for 1 minute, followed by a polymerization process at 72° C. for 7 minutes. After the PCR was completed, DNAs were detected by electrophoresis with 3% agarose gel containing TAE buffer (40 mM Tris-acetate; 1 mM EDTA, pH 8.0) with 0.5 µg/ml etidium bromide by using 5 µl of the reaction mixture. This is shown in FIG. 6.

In what follows, the nine kinds of polyamine (A–I) used in the experiments are indicated as follows:

| | | |
|---|---|---|
| A: | Ethylenediamine | $H_2N(CH_2)_2NH_2$ |
| B: | Trimethylenediamine | $H_2N(CH_2)_3NH_2$ |
| C: | Putrescine | $H_2N(CH_2)_4NH_2$ |
| D: | Diethylenetriamine | $H_2N(CH_2)_2NH(CH_2)_2NH_2$ |
| E: | Spermidine | $H_2N(CH_2)_3NH(CH_2)_4NH_2$ |
| F: | Triethylenetetramine | |
| | | $H_2N(CH_2)_2NH(CH_2)_2NH(CH_2)_2NH_2$ |
| G: | Spermine | |
| | | $H_2N(CH_2)_3NH(CH_2)_4NH(CH_2)_3NH_2$ |
| H: | Tetraethylenepentamine | |
| | | $H_2N(CH_2)_2NH(CH_2)_2NH(CH_2)_2NH(CH_2)_2NH_2$ |
| I: | Pentaethylenehexamine | |
| | | $H_2N(CH_2)_2NH(CH_2)_2NH(CH_2)_2NH(CH_2)_2NH(CH_2)_2NH_2$ | and the numerals (1–7) in FIG. 6 indicate the final concentration of polyamine as follows:
1: 8 mM
2: 4 mM
3: 2 mM
4: 1 mM
5: 0.5 mM
6: 0.25 mM
7: 0.125 mM.

If comparisons are made between polyamines having the same number of amino groups (A vs B vs C, D vs E, F vs G), it is found that the smaller (greater) the number of carbon chains between amino groups, the higher (lower) the concentration at which effects are significant on PCR-inhibiting substances derived from blood. If Spermine is used, however, no such effect was observed whether the concentration was high or low, and the effect became prominently weaker if the number of amino groups was 6 or greater (I). According to the aforementioned report by Wan and Wilkins, the optimum concentration of Spermidine is 0.2 to 1 mM if use is made of "DNA isolated from plants". The optimum concentration of 0.5 to 2 mM according to the present investigation is relatively higher. No amplification was observed at concentration of 0.25 mM.

This indicates that the effect of reducing the PCR inhibition due to substances derived from human blood varies, depending on the number of amino groups in polyamine and the number of carbon chains between amino groups. In view thereof, the next Experiment was carried out by setting polyamine concentration at 2 mM (at which effects were observable with all polyamines except Spermine) and by varying the number of target DNA.

Experiment No. 2 (With Human Blood)

White blood cells were obtained by taking 14 µl ($7\times10^4$ WBC) of human blood, centrifuging it and removing therefrom the supernatant. Various polyamines (2 mM), HIV DNA (1000, 100 10 and 0 copies/tube) and PCR core solution were added to the white blood cells thus collected for carrying out PCR (total 50 µl ). The same PCR core solution was used as in Experiment No. 1. The PCR was carried out for 40 cycles under the same conditions as in Experiment 1, and the amplification detection was carried out as in Experiment No. 1. The result is shown in FIG. 7 wherein the numerals indicate the number of HIV DNA copies per tube as follows:
1: 1000 copies/tube
2: 100 copies/tube
3: 10 copies/tube
4: 0 copy/tube Between D and E, both having 3 amino groups, D with 2 carbon chains between each pair of amino groups was about 10 times more sensitive than E having 3 and 4 carbon chains between amino groups, allowing 10 copies of DNA to be detected. Between F and G, both having 4 amino groups, F with 2 carbon chains between each pair of amino groups allowed 10 copies of DNA to be detected, but DNA could not be detected with G having 3 and 4 carbon chains between its amino groups. With H and I having respectively 5 and 6 animo groups and 2 carbon chains each between the amino groups, amplification bands were detected with the number of HIV DNA copies as low as 10. With A, B and C having 2 amino groups and respectively 2, 3 and 4 carbon chains in between, amplification bands were detected with the number of HIV DNA copies as low as 10.

Experiment No. 2 did not show which polyamines have prominent effects, but one could learn therefrom that different effects are obtained, depending on the kind of polyamine.

Experiment No. 3 (With Human Feces)

A sample was obtained by making a 1% suspension of human feces in TE buffer (10 mM Tris-HCl, pH 8.0; 1 mM EDTA) and subjecting it to a heat treatment at 95° C. for 10 minutes. PCR was carried out by adding various kinds of polyamine, DNA from heat-labile enterotoxin(LT)-producing Escherichia coli (100 copies/tube) and PCR core solution to 5 µl of supernatant of samples after centrifugation (final volume=50 µl). The primers for the PCR were oligonucleotides (ELT-1 and ELT-2, products of Takara Shuzo Co., Ltd. of Japan) homologous to plus and minus chains, respectively, which are located in LT coding region and what gives 264 bp PCR products. The PCR core solution was the same as used in Experiment No. 1 except that ELT-1 and ELT-2 were used as primer. After a preheating process of 1.5 minutes at 94° C., PCR was carried out for 50 cycles under the conditions of 94° C. for 1 minute, 55° C. for 1 minute and 72° C. for 1 minute, followed by a polymerization process at 72° C. for 7 minutes. The detection was carried out as in Experiment No. 1. The result is shown in FIG. 8 wherein the numerals indicate the concentration of polyamine as follows:
1: 4 mM
2: 2 mM
3: 1 mM
4: 0.5 mM
5: 0.25 mM
6: 0.125 mM If comparisons are made between polyamines having the same number of amino groups (D vs E, F vs G), it is found, as when blood is used, that the smaller (greater) the number of carbon chains between amino groups, the higher (lower) the concentration at which the effect is great against PCR-inhibiting substances derived from feces. Unlike the situation where blood is used, some effects are observed even if Spermine is used, but no effect was observed when use was made of polyamine with two amino groups (A, B and C). The effect was not any weaker with polyamine having 6 amino groups (I). The optimum concentration of Spermidine when the PCR is carried out is 0.5 to 2 mM, as in the case where blood is used.

This indicates that the kinds of polyamine which can effectively reduce the inhibition of PCR by samples derived from feces may be different from those effective in reducing the inhibition of PCR by samples derived from blood. In view thereof, the next Experiment was carried out by setting polyamine concentration at 1 mM (at which effects were observable with all polyamine samples except those containing 2 amino groups) and by varying the sample concentration.

Experiment No. 4 (With Human Feces)

A sample was obtained by making an 8% suspension of human feces in TE buffer and subjecting it to a heat treatment at 95° C. for 10 minutes. PCR was carried out by adding various kinds of polyamine (1 mM), DNA from LT Escherichia coli (100 copies/tube) and PCR core solution to variously diluted supernatant of sample (final volume=50 µl ). The PCR core solution was the same as used in Experiment No. 3, and PCR was carried out for 40 cycles under the same conditions as in Experiment 3. The detection was carried out as in Experiment No. 1. The result is shown in FIG. 9 wherein the numerals indicate the concentration of feces as follows:
1: 0.8%
2: 0.4%
3: 0.2%
4: 0.1%
5: 0.05%
6: 0.025%
7: 0.013%

If use is made of polyamine with 2 amino groups and 2 carbon chains therebetween (A), the maximum concentration of feces at which amplification bands are observed is 4 times as large as in the case of no addition of polyamine (J)

and it is twice as large in the case of polyamine with 3 or 4 carbon chains between amino groups (B, C). If polyamines with 3 amino groups are compared, D with 2 carbon chains between amino groups shows brighter and thicker amplification bands than E with 3 and 4 carbon chains between the amino groups. The maximum concentration of feces allowing amplification bands to be observed was 8 times greater with D and E than with J. As for polyamines with 4 amino groups, the maximum concentration of feces at which amplification bands were observable with F (with 2 carbon chains between amino groups) was 16 times greater than with J. With G (with 3 and 4 carbon chains between amino groups), only thin amplification bands were observable when the concentration of feces was 4 times greater than the maximum concentration of feces at which amplification bands were observable with J. With H and I having 5 or 6 amino groups and 2 carbon chains between the amino groups, the results were similar to those obtained with F.

In summary, it is learned that inhibition of PCR due to feces is strongly reduced as the number of amino groups is increased and the number of carbon chains between the amino groups is reduced for the polyamine to be used. In other words, good results are obtained with F, H and I having 4 or more amino groups and 2 carbon chains between them but hardly any effect was observable with B or C having 2 amino groups and 3 or 4 carbon chains therebetween.

Experiment No. 5 (With Human Urine)

Human urine was used without refinement as sample. PCR was carried out by adding various polyamines, DNA from LT Escherichia coli (100 copies/tube) and PCR core solution to 1 µl of the sample (final volume=50 µl). The PCR core solution was the same as used in Experiment No. 3, and the PCR and the detection were carried out as in Experiment No. 4. The result is shown in FIG. 10 wherein the numerals indicate the polyamine concentration as follows:

1: 8 mM
2: 4 mM
3: 2 mM
4: 1 mM
5: 0.5 mM
6: 0.25 mM
7: 0.125 mM
8: 0 mM

If comparisons are made between polyamines having the same number of amino groups (B vs C, D vs E, F vs G), it is found that the smaller the number of carbon chains between amino groups, the higher the concentration at which the effect could be observed against PCR inhibiting substances derived from urine. If the number of amino groups is large (I), effect of polyamine ceases to be observable at high concentrations. The next experiment was carried out by fixing the concentration of polyamine at 2 mM and varying the amount of the sample.

Experiment No. 6 (With Human Urine)

Human urine was used without refinement as sample. PCR was carried out by adding polyamine (2 mM), DNA from LT Escherichia coli (100 copies/tube) and PCR core solution to various amounts of the sample (final volume=50 µl). The PCR core solution was the same as used in Experiment No. 3, and the PCR and the detection were carried out as in Experiment No. 4. The result is shown in FIG. 11 wherein the numerals indicate the amount of the sample as follows:

1: 8 µl
2: 4 µl
3: 2 µl
4: 1 µl
5: 0.5 µl
6: 0 µl

When polyamine was not added, PCR products specific to LT genes could be detected in the presence of 1 µl of urine but could not be detected in the presence of 2 µl of urine. Even if polyamine is added, PCR was inhibited, independent of the kind of the added polyamine, when 2 µl or 4 µl of urine was present. In summary, polyamine could hardly be effective against the PCR inhibition by substances derived from urine. If Spermine is additionally used (G), this tends to increase the PCR inhibition by substances derived from urine.

The following conclusions may be drawn from the series of experiments described above. Firstly, if human blood and/or feces are used as sample, the effect of polyamine to reduce PCR inhibition by such sample becomes stronger as the number of carbon chains between the amino groups is reduced. As for the number of amino groups in polyamine, it may be secondly concluded that mutually opposing results are obtained. With blood samples, the effect of reducing PCR inhibition becomes stronger as the number of amino groups decreases. With feces samples, the effect of reducing PCR inhibition becomes stronger as the number of amino groups increases. Experiment No. 3 and FIG. 8, for example, suggest that a smaller polyamine concentration is sufficient if the number of amino groups in the polyamine is larger because migration bands in electrophoresis begin to appear even at 0.125 mM (Lane 6 in FIG. 8). If the number of amino groups is 3 or less (A–E in FIG. 8), the polyamine concentration must be 0.25 mM or greater, since migration bands appear only up to Lane 5 (concentration of 0.25 mM) but migration bands are discernible even in Lane 6 (concentration of 0.125 mM) if the number of amino groups is 4 or greater (F–I in FIG. 8). Thirdly, it is noted that hardly any effect was observed with Spermine with blood and feces samples. Fourthly, hardly any effect was observed with trimethylenediamine or putrescine against feces samples. Against urine samples, it may be noted fifthly that hardly any effect was observed with any polyamine. If Spermine is additionally used, the effect of PCR inhibition due to materials derived from the urine tends to increase.

In summary, if an animal substance (such as blood, feces or urine) is present, there are both situations where the effect of polyamine is clearly observable and where it is hardly observable, and this difference depends on the type of the sample which is present. Even in situations where the effect is clearly observable, the type of polyamine having such a clearly observable effect varies, depending on the kind of the sample present. If a sample of blood or feces is present, the optimum concentration of Spermidine is 0.5 to 2 mM, which is much higher than the concentration reported in the aforementioned article by Wan and Wilkins.

Thus, the present invention makes it possible to reduce the inhibition of nucleic acid synthesis by the existence of impurities in the sample and hence to efficiently synthesize target genes from a sample obtained from a living organism or the environment.

What is claimed is:

1. A method of amplifying a target nucleic acid found in animal feces, said method consisting of the steps of:

suspending a sample of animal feces in an aqueous solution, thereby forming an animal feces solution;

adding an aliquot of said animal feces solution to a solution containing reagents necessary for PCR amplification to form a PCR amplification system comprising a polyamine in an amount of 0.125 nM–4 mM, said reagents comprising said polyamine; and causing PCR to be carried out in said PCR amplification system, whereby the target nucleic acid found in the animal feces is amplified.

2. The method of claim 1 wherein said animal feces includes human feces.

* * * * *